United States Patent
Ozawa et al.

(10) Patent No.: US 12,171,612 B2
(45) Date of Patent: Dec. 24, 2024

(54) IMAGING ASSISTING APPARATUS AND STORAGE MEDIUM STORING THEREIN IMAGING ASSISTING COMPUTER PROGRAM

(71) Applicant: CANON MEDICAL SYSTEMS CORPORATION, Otawara (JP)

(72) Inventors: Shinya Ozawa, Nasushiobara (JP); Kiyomi Oshima, Nasushiobara (JP); Kensuke Shinoda, Otawara (JP); Gaku Kaneda, Sakura (JP); Hidetaka Konta, Utsunomiya (JP); Yuto Ono, Nasushiobara (JP); Yoshiharu Ohiwa, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 595 days.

(21) Appl. No.: 17/087,780

(22) Filed: Nov. 3, 2020

(65) Prior Publication Data
US 2021/0137481 A1 May 13, 2021

(30) Foreign Application Priority Data

Nov. 8, 2019 (JP) ................................. 2019-203383

(51) Int. Cl.
| | | |
|---|---|---|
| *G16H 50/20* | (2018.01) | |
| *A61B 5/00* | (2006.01) | |
| *A61B 5/055* | (2006.01) | |
| *A61B 6/00* | (2024.01) | |
| *G06T 7/00* | (2017.01) | |
| *G16H 30/40* | (2018.01) | |
| *A61B 6/03* | (2006.01) | |

(52) U.S. Cl.
CPC ............ *A61B 6/545* (2013.01); *A61B 5/0037* (2013.01); *A61B 5/0042* (2013.01); *A61B 5/743* (2013.01);
(Continued)

(58) Field of Classification Search
CPC ..... A61B 5/055; A61B 5/0037; A61B 5/0033; A61B 5/004–0044; G01R 33/44;
(Continued)

(56) References Cited

U.S. PATENT DOCUMENTS

| | | | |
|---|---|---|---|
| 2011/0206260 A1* | 8/2011 | Bergmans ............ | G01R 33/543 382/131 |
| 2011/0211744 A1 | 9/2011 | Darrow et al. | |

(Continued)

FOREIGN PATENT DOCUMENTS

| | | |
|---|---|---|
| CN | 106821408 A | 6/2017 |
| EP | 3 546 973 A1 | 10/2019 |

(Continued)

OTHER PUBLICATIONS

Japanese Office Action issued May 9, 2023 in Japanese Patent Application No. 2019-203383, 2 pages.
(Continued)

*Primary Examiner* — Carolyn A Pehlke
(74) *Attorney, Agent, or Firm* — Oblon, McClelland, Maier & Neustadt, L.L.P.

(57) ABSTRACT

An imaging assisting apparatus according to an embodiment is configured to assist imaging of a medical image diagnosis apparatus that performs a series of medical examinations including a plurality of scan protocols, the imaging assisting apparatus including a processing circuit. The processing circuit is configured to obtain data acquired according to one or more already-executed scan protocols among the plurality of scan protocols. The processing circuit is configured to perform one of the following when a disease or a region suspected of a disease is extracted from the data: controlling a scan protocol which is among the plurality of scan protocols and later than the already-executed scan protocols; and generating reference information related to controlling a
(Continued)

scan protocol which is among the plurality of scan protocols and later than the already-executed scan protocols.

15 Claims, 5 Drawing Sheets

(52) U.S. Cl.
CPC .......... *A61B 6/5217* (2013.01); *G06T 7/0012* (2013.01); *G16H 30/40* (2018.01); *G16H 50/20* (2018.01); *A61B 5/055* (2013.01); *A61B 6/032* (2013.01); *G06T 2200/24* (2013.01); *G06T 2207/10088* (2013.01); *G06T 2207/20081* (2013.01)

(58) Field of Classification Search
CPC .... G01R 33/54; G01R 33/543; G01R 33/546; G01R 33/56366
See application file for complete search history.

(56) References Cited

U.S. PATENT DOCUMENTS

| | | | | |
|---|---|---|---|---|
| 2015/0216429 A1* | 8/2015 | Miyazaki | ............... | G06T 7/0016 600/419 |
| 2016/0128606 A1* | 5/2016 | Sakuragi | ................ | A61B 5/055 600/415 |
| 2017/0108568 A1 | 4/2017 | Sueoka | | |
| 2019/0310333 A1* | 10/2019 | Ham | ................... | G01R 33/3403 |
| 2020/0160965 A1* | 5/2020 | Lyman | ................... | G06F 18/217 |
| 2020/0163550 A1* | 5/2020 | Igarashi | ................. | G16H 40/63 |

FOREIGN PATENT DOCUMENTS

| | | | |
|---|---|---|---|
| JP | 2002-112996 | A | 4/2002 |
| JP | 2005-198798 | A | 7/2005 |
| JP | 2010-29481 | A | 2/2010 |
| JP | 2010-29482 | A | 2/2010 |
| JP | 2017-77301 | A | 4/2017 |

OTHER PUBLICATIONS

Japanese Office Action issued Oct. 10, 2023 in Japanese Patent Application No. 2019-203383, 2 pages.
Combined Chinese Office Action and Search Report issued Jul. 3, 2023, in corresponding Chinese Patent Application No. 202011229269.9 (with English Translation of Category of Cited Documents), 9 pages.
Japanese Office Action issued in Japanese Patent Application No. 2019-203383 on Feb. 13, 2024, (w/ partial English translation).
Chinese Office Action issued in Chinese Patent Application No. 202011229269.9 on Feb. 18, 2024.

\* cited by examiner

| Locator |
| --- |
| Map |
| Shimming |
| SCAN PROTOCOL $\alpha$ |

IMAGING ASSISTING APPARATUS AND STORAGE MEDIUM STORING THEREIN IMAGING ASSISTING COMPUTER PROGRAM

CROSS-REFERENCE TO RELATED APPLICATIONS

This application is based upon and claims the benefit of priority from Japanese Patent Application No. 2019-203383, filed on Nov. 8, 2019; the entire contents of which are incorporated herein by reference.

FIELD

Embodiments described herein relate generally to an imaging assisting apparatus and a storage medium storing therein an imaging assisting computer program (hereinafter, simply "imaging assisting program").

BACKGROUND

Conventionally, for medical examinations using a medical image diagnosis apparatus such as a Magnetic Resonance Imaging (MRI) apparatus, a technique may be used by which a large number of images are taken so that the obtained images are successively displayed on a display device.

Even when the above technique is used, it is difficult for the user to determine during the imaging process whether or not a lesion has been found or an image rendering a lesion has successfully been acquired, from the large number of images. For this reason, it is a common practice to execute a plurality of scan protocols that were set at the beginning of the medical examination, to the end.

In some situations, however, images that are not necessary for interpretation may be taken in unnecessary medical examinations, which increases the number of images to be checked by an interpreting doctor. In those situations, the work load of the interpreting doctor becomes extremely large. In addition, when an urgent procedure needs to be performed on the patient, it is desirable to shorten the time required by the medical examinations.

DETAILED DESCRIPTION

An imaging assisting apparatus according to an embodiment is configured to assist imaging of a medical image diagnosis apparatus that performs a series of medical examinations including a plurality of scan protocols, the imaging assisting apparatus including a processing circuit. The processing circuit is configured to obtain data acquired according to one or more already-executed scan protocols among the plurality of scan protocols. The processing circuit is configured to perform one of the following when a disease or a region suspected of a disease is extracted from the data: controlling a scan protocol which is among the plurality of scan protocols and later than the already-executed scan protocols; and generating reference information related to controlling a scan protocol which is among the plurality of scan protocols and later than the already-executed scan protocols.

First Embodiment

An imaging assisting apparatus according to a first embodiment will be explained below, with reference to the accompanying drawings.

Figure 1:
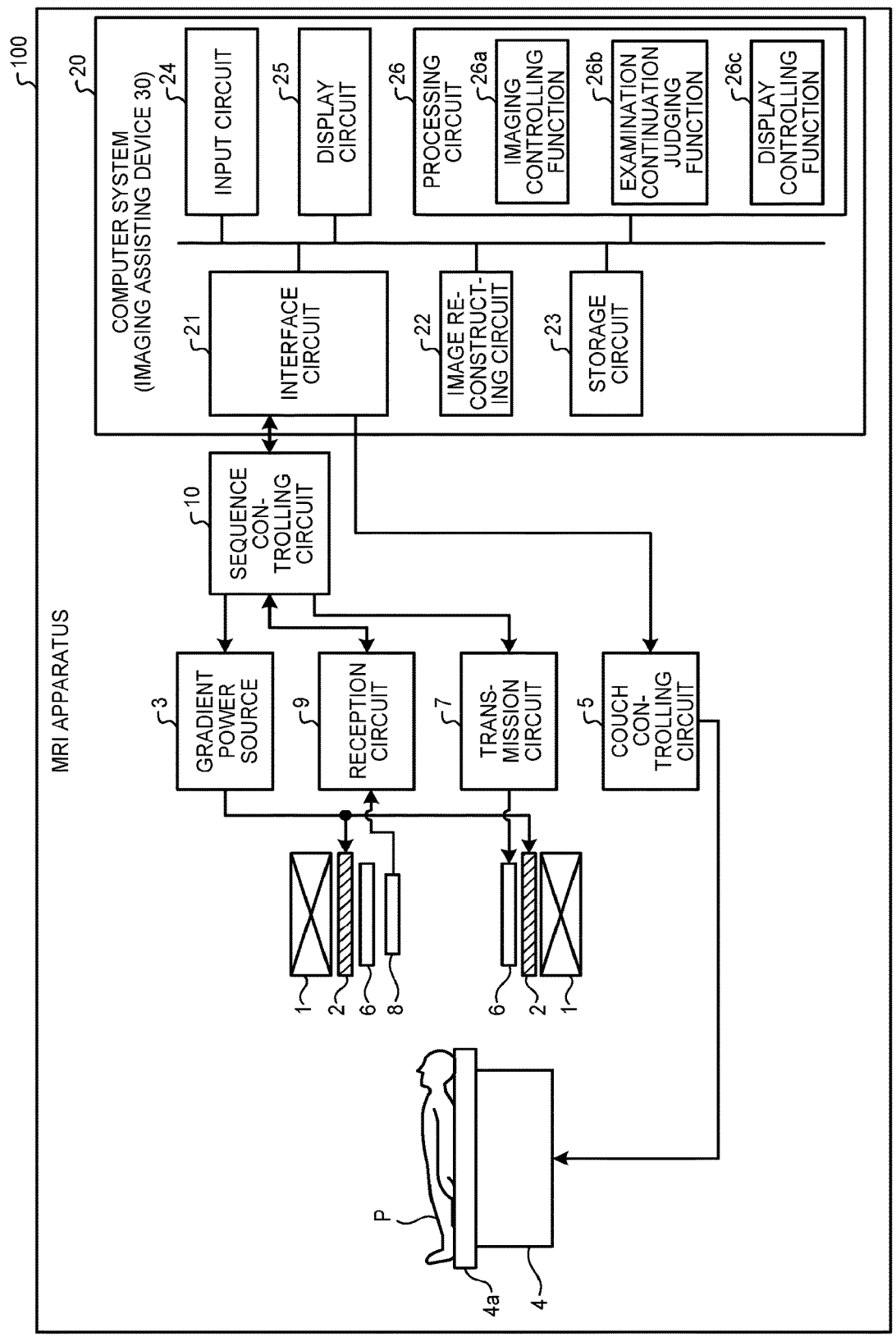
FIG. 1 is a block diagram illustrating an exemplary configuration of a magnetic resonance imaging apparatus 100 having incorporated therein an imaging assisting apparatus 30 according a first embodiment.

FIG. 1 is a block diagram illustrating an exemplary configuration of a magnetic resonance imaging apparatus 100 having incorporated therein an imaging assisting apparatus 30 according to the first embodiment. As illustrated in FIG. 1, the magnetic resonance imaging apparatus 100 includes: a static magnetic field magnet 1, a gradient coil 2, a gradient power source 3, a couch 4, a couch controlling circuit 5, a whole body Radio Frequency (RF) coil unit 6, a transmission circuit 7, a local RF coil unit 8, a reception circuit 9, a sequence controlling circuit 10, and a computer system 20. The computer system 20 includes an interface circuit 21, an image reconstructing circuit 22, a storage circuit 23, an input circuit 24, a display circuit 25, and a processing circuit 26. The magnetic resonance imaging apparatus 100 does not include an examined subject (hereinafter "patient") P (e.g., a human body).

The imaging assisting apparatus 30 according to the first embodiment is, for example, realized by the interface circuit 21, the image reconstructing circuit 22, the storage circuit 23, the input circuit 24, the display circuit 25, and an examination continuation judging function 26b of the processing circuit 26, that are included in the computer system 20. A display controlling function 26c may also be included, as necessary.

The static magnetic field magnet 1 is a magnet formed to have a hollow and circular cylindrical shape, for example, and is configured to generate a uniform static magnetic field in the space inside thereof. The circular cylindrical shape may have an oval cross-section orthogonal to the axis thereof.

The gradient coil 2 is a coil formed to have a hollow and circular cylindrical shape and is configured to generate a gradient magnetic field.

The gradient power source 3 is configured to supply an electric current to the gradient coil 2.

The couch 4 is configured, under control of the couch controlling circuit 5, to insert a couchtop 4a to the inside of an image taking space while the patient P is placed thereon.

The couch controlling circuit 5 is a processor configured, under the control of the computer system 20, to move the couchtop 4a in longitudinal directions and up-and-down directions by driving the couch 4.

The whole body RF coil unit 6 is arranged on the inside of the gradient coil 2. The whole body RF coil unit 6 is configured to generate a radio frequency magnetic field from a plurality of coil elements, by receiving a supply of a transmission-purpose radio frequency pulse from the transmission circuit 7. Further, the whole body RF coil unit 6 is configured to receive a magnetic resonance signal (hereinafter, "MR signal") emitted from the patient P as a result of excitation by the radio frequency magnetic field.

The transmission circuit 7 is configured to supply an RF pulse corresponding to a Larmor frequency determined by the type of a target atomic nucleus and the magnetic field intensities, to the whole body RF coil unit 6.

The local RF coil unit 8 has a shape and a size corresponding to an imaged site of the patient P and is placed in a position corresponding to the imaged site. By using a plurality of coil elements, the local RF coil unit 8 is configured to receive the MR signal that is emitted from the patient P as a result of the excitation by the radio frequency magnetic field and to output the received MR signal to the reception circuit 9. In this situation, the local RF coil unit 8 does not necessarily have to be exclusively for reception and may be configured to be for both transmission and reception or exclusively for transmission.

The sequence controlling circuit 10 is configured to perform an imaging process on the patient P, by controlling the gradient power source 3, the transmission circuit 7, and the reception circuit 9 on the basis of sequence information transmitted thereto from the computer system 20. The sequence controlling circuit 10 may be realized by using a processor or may be realized by using a combination of software and hardware.

The sequence information is information defining a pulse sequence executed during a medical examination (hereinafter, "examination") performed by the magnetic resonance imaging apparatus 100. The sequence information defines: the intensity of the electric current to be supplied by the gradient power source 3 to the gradient coil 2 and the timing with which the electric current is to be supplied; the intensity of the RF pulse to be transmitted by the transmission circuit 7 to the whole body RF coil unit 6 or to the local RF coil unit 8 and the timing with which the RF pulse is to be applied; the timing with which the MR signal is to be detected by the reception circuit 9, and the like.

Further, the sequence information is generated by the computer system 20, on the basis of image taking conditions designated by an operator, such as various types of image taking parameters including, for example, Repetition Time (TR), Echo Time (TE), the number of slices, slice positions, slice thicknesses, a matrix, a Field Of View (FOV), and a sampling density indicating the ratio of sampled k-space data to fully-sampled k-space data.

The computer system 20 is configured to control the entirety of the magnetic resonance imaging apparatus 100, to acquire data, and to reconstruct images. More specifically, the computer system 20 is configured to control the sequence controlling circuit 10 and the couch controlling circuit 5.

The interface circuit 21 is configured to transmit the sequence information to the sequence controlling circuit 10 and to receive MR data from the sequence controlling circuit 10. Further, when having received the MR data, the interface circuit 21 is configured to store the received MR data into the storage circuit 23.

The image reconstructing circuit 22 is a processor configured to reconstruct an image from the MR data transmitted thereto from the sequence controlling circuit 10 and to store the reconstructed image into the storage circuit 23. The image reconstructing circuit 22 is configured to arrange the MR data sent thereto from the sequence controlling circuit 10 as an imaged result, according to a phase encoding amount and a frequency encoding amount applied by the abovementioned gradient magnetic fields. The arranged MR data will be referred to as k-space data. An MR image is generated by performing a reconstructing process (e.g., Fourier transform) on the k-space data.

The storage circuit 23 is configured to store therein various types of programs. For example, the storage circuit 23 is realized by using a semiconductor memory element such as a Random Access Memory (RAM), a flash memory, or the like, or a hard disk, an optical disk, or the like. The storage circuit 23 is also used as non-transitory storage medium configured with hardware.

The input circuit 24 is configured to receive various types of instructions and inputs of information from the operator such as a medical doctor or a radiological technologist. The input circuit 24 is realized by using, for example, a trackball, a switch button, a mouse, a keyboard, and/or the like. The input circuit 24 is connected to the processing circuit 26 and is configured to convert input operations received from the operator into electrical signals and to output the electrical signals to the processing circuit 26.

Under the control of the processing circuit 26, the display circuit 25 is configured to display various types of Graphical User Interfaces (GUIs), Magnetic Resonance (MR) images, and the like.

The processing circuit 26 is a processor configured to control the entirety of the magnetic resonance imaging apparatus 100. More specifically, by employing an imaging controlling function 26a, the processing circuit 26 is configured to generate the sequence information on the basis of the image taking conditions input by the operator via the input circuit 24 and to control the imaging process by transmitting the generated sequence information to the sequence controlling circuit 10.

When a disease or a region suspected of a disease has been extracted from the obtained data, the processing circuit 26 is configured, by employing the examination continuation judging function 26b, to control the scan protocols later than the scan protocols under which the imaging processes have already been executed (hereinafter, "already-executed scan protocols"). Further, when a disease or a region suspected of a disease has been extracted from the obtained data, the processing circuit 26 is configured, by employing the examination continuation judging function 26b, to generate reference information related to controlling the scan protocols later than the already-executed scan protocols. In the present embodiment, the information related to the disease or the region suspected of a disease extracted from the obtained data may be referred to as "information related to diseases".

Further, by employing the examination continuation judging function 26b, the processing circuit 26 is configured to obtain the data acquired according to the already-executed scan protocols among the plurality of scan protocols and to generate the reference information related to cancelling the execution of the imaging processes according to the not-yet-finished scan protocols among the plurality of scan protocols, on the basis of the information related to diseases extracted from the obtained data.

In the present embodiment, a set made up of a plurality of scan protocols being set for one examination will be referred to as an "examination protocols". According to each scan protocol, an imaging process is performed according to one pulse sequence, for example.

Further, "reference information related to cancelling the execution of the imaging processes according to the not-yet-finished scan protocols (which hereinafter may simply be referred to as 'reference information')" denotes information used by a user for judging whether or not the imaging processes according to the not-yet-finished scan protocols continue to be executed. In a specific example, the reference information includes at least information inquiring the user whether or not the imaging process according to at least one not-yet-finished scan protocol at the current point in time needs to be continued. Further, the reference information may include a list of all the not-yet-finished scan protocols at the current point in time or information inquiring the user whether or not each of the scan protocols in the list needs to be deleted, and the like.

Further, by employing the display controlling function 26c, the processing circuit 26 is configured to exercise control so as to cause the display circuit 25 to display the generated MR image. Further, by employing the display controlling function 26c, the processing circuit 26 is configured to cause the display circuit 25 to display a GUI including the reference information.

With reference to FIG. 1, the example was explained in which the single processor (i.e., the processing circuit 26) is configured to realize the processing functions implemented by the imaging controlling function 26a, the examination continuation judging function 26b, and the display controlling function 26c; however, another arrangement is also acceptable in which a processing circuit is structured by combining together a plurality of independent processors, so that the functions are realized as a result of the processors executing the programs. Further, with reference to FIG. 1, the example was explained in which the single storage circuit (i.e., the storage circuit 23) stores therein the programs corresponding to the processing functions; however, another arrangement is also acceptable in which a plurality of storage circuits 23 are provided in a distributed manner, so that the processing circuit 26 reads a corresponding program from each of the individual storage circuits 23.

Figure 2:
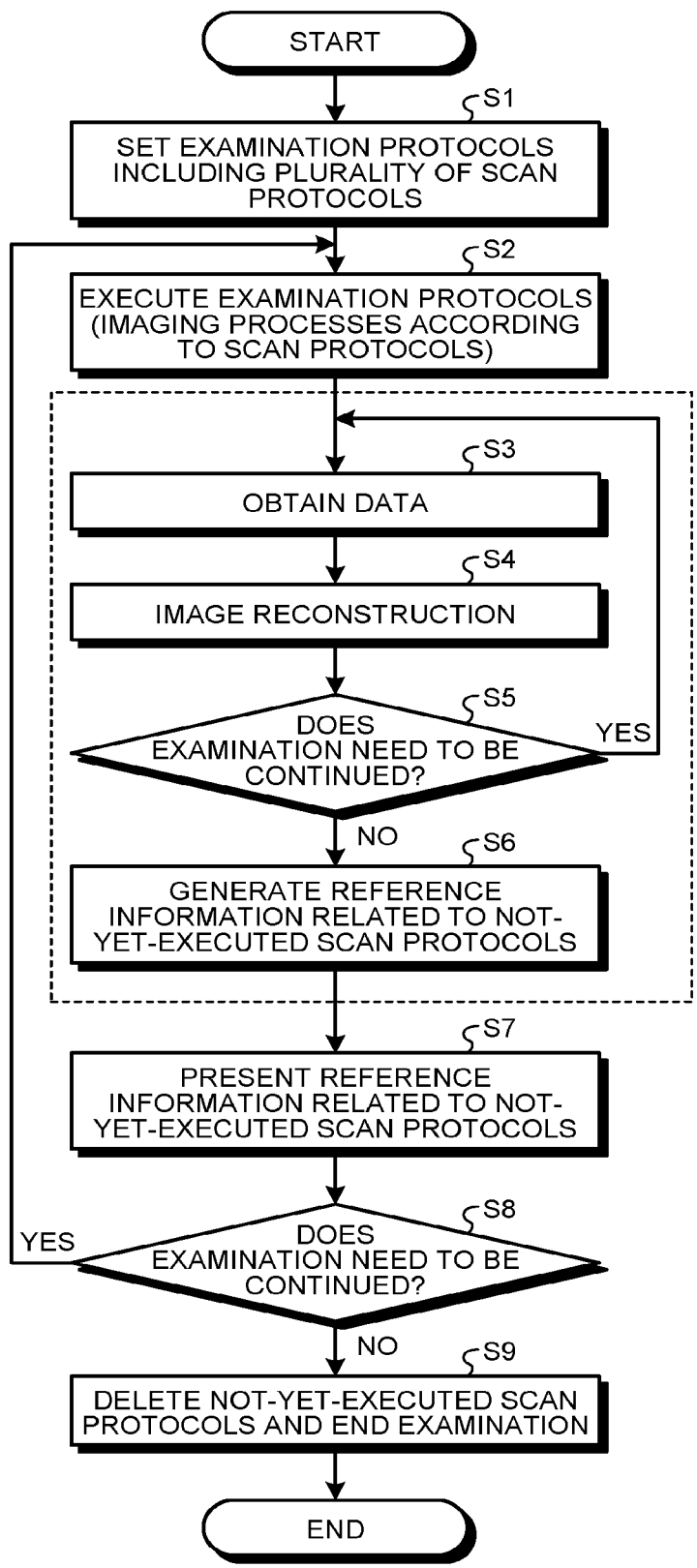
FIG. 2 is a flowchart illustrating an example of a flow in an imaging assisting process performed on the magnetic resonance imaging apparatus 100 by the imaging assisting apparatus 30 according to the first embodiment.

FIG. 2 is a flowchart illustrating a flow in an imaging assisting process performed on the magnetic resonance imaging apparatus 100 by the imaging assisting apparatus 30 according to the first embodiment.

In the following sections, to explain the processes more specifically, an example will be used in which an examination using the magnetic resonance imaging apparatus 100 is performed on a patient suspected of having a cerebral disease with high urgency such as a cerebral infarction.

As illustrated in FIG. 2, to begin with, on the basis of an input from the input circuit 24, the processing circuit 26 sets examination protocols including a plurality of scan protocols, by employing the imaging controlling function 26a (step S1).

Figure 3:
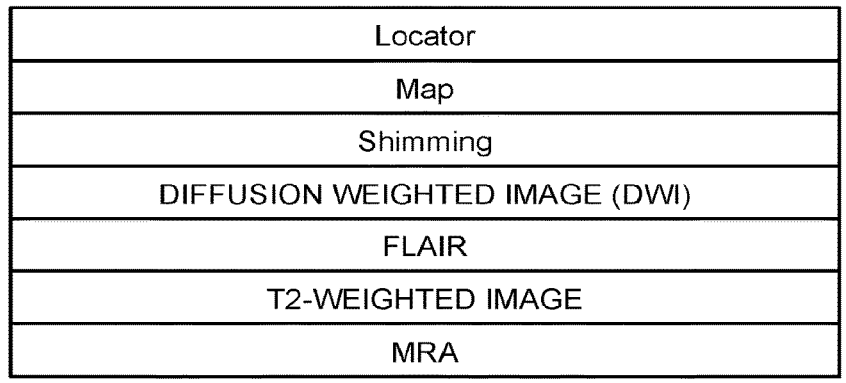
FIG. 3 is a drawing illustrating examples of examination protocols set at step S1 in FIG. 2.

FIG. 3 is a drawing illustrating examples of the examination protocols set at step S1. In FIG. 3, the "Locator" is the name of a scan protocol defining various types of image taking conditions to be used when acquiring a locator image used for determining an imaged region of a diagnosis image. Further, the "Map" is the name of a scan protocol defining various types of image taking conditions to be used when acquiring a sensitivity map indicating the sensitivity of each of the plurality of coil elements included in the local RF coil unit 8. Further, the "Shimming" is the name of a scan protocol defining various types of image taking conditions of shimming used for correcting a static magnetic field distribution and setting a center frequency. The "Diffusion Weighted Image (DWI)" is the name of a scan protocol defining various types of image taking conditions to be used when taking a Diffusion Weighted Image (DWI) used for an image diagnosis process. The "FLAIR" is the name of a scan protocol defining various types of image taking conditions to be used when taking an MR image for an image diagnosis process by implementing a FLAIR method. The "T2-weighted image" is the name of a scan protocol defining various types of image taking conditions to be used when taking a T2-weighted image for an image diagnosis process. The "MRA" is the name of a scan protocol defining various types of image taking conditions to be used when taking a Magnetic Resonance Angiography (MRA) image for an image diagnosis process.

Subsequently, by employing the imaging controlling function 26a, the processing circuit 26 sequentially performs the imaging processes according to the examination protocols set at step S1 (step S2).

For example, in the example in FIG. 3, by employing the imaging controlling function 26a, the processing circuit 26 obtains information necessary for the acquisitions and corrections of the diagnosis images, by executing the "Locator", the "Map", and the "Shimming" in the stated order and further takes the diagnosis images in the order of a "DWI", a "FLAIR" image, a "T2-weighted image" and an "MRA" image.

The image reconstructing circuit 22 sequentially obtains pieces of MR data taken according to the scan protocols at step S2 (step S3) and generates MR images by performing an image reconstructing process (step S4).

After that, by employing the examination continuation judging function 26b, the processing circuit 26 sequentially receives the reconstructed MR images from the image reconstructing circuit 22 and, by using the received MR images, judges whether or not the imaging processes according to the not-yet-finished scan protocols need to be performed, i.e., whether or not the examination needs to be continued (step S5). For example, by employing the examination continuation judging function 26b, the processing circuit 26 judges whether or not a disease or a region suspected of a disease is present in the received MR images, by using a template matching process, a learning model with AI, or the like and judges whether or not the examination needs to be continued on the basis of the judgment result. Further, for example, by employing the examination continuation judging function 26b, the processing circuit 26 judges whether or not the examination needs to be continued, by using inputs of the judgment result as to whether or not a disease or a region suspected of a disease is present, a type of disease detected by implementing a predetermined method, a database of a certain type of images necessary for diagnosing the detected type of disease, and/or the like. The database of the certain type of images includes a decision tree or a machine learning model. In this situation, unnecessary types of images are images that are not to be used for the diagnosis process, but are used for calibration of the magnetic resonance imaging apparatus 100, or the like.

Further, when judging whether or not the examination needs to be continued by using the MR images, information other than the MR images obtained during the examination may be used. For example, whether or not the examination needs to be continued may be judged by referring to a definitive diagnosis image, a basis of a diagnosis, and/or observations from the past. Further, it is also acceptable to use a locator image to judge whether or not a disease or a region suspected of a disease is present.

The process of judging whether or not the examination needs to be continued at step S5 may partially be performed on the not-yet-finished scan protocols. In other words, there is a possibility that the not-yet-finished scan protocols may include both those that need to be executed and those that do not need to be executed. Accordingly, an arrangement may be made so that, even when one of the scan protocols is determined to be an unnecessary examination, the examinations of the other not-yet-finished scan protocols can be determined to be continued. For example, let us discuss a situation where, among the examination protocols illustrated in FIG. 3, while the imaging process according to the scan protocol "Diffusion Weighted Image (DWI)" is being executed, it is determined at step S5 that the examination "does not need" to be continued. In that situation, among the not-yet-finished scan protocols, the necessity for the continuation may partially be determined by indicating that the "FLAIR" and the "T2-weighted image" do not need to be continued, while the "MRA" needs to be continued.

When it is determined that the examination "needs" to be continued (step S5: Yes), the processing circuit 26 returns to step S3.

On the contrary, when it is determined that the examination "does not need" to be continued (step S5: No), the processing circuit 26 generates, by employing the examination continuation judging function 26*b*, reference information related to cancelling the execution of the imaging processes according to the not-yet-finished scan protocols (step S6). Further, by employing the display controlling function 26*c*, the processing circuit 26 presents the generated reference information via the display circuit (step S7).

Figure 4:
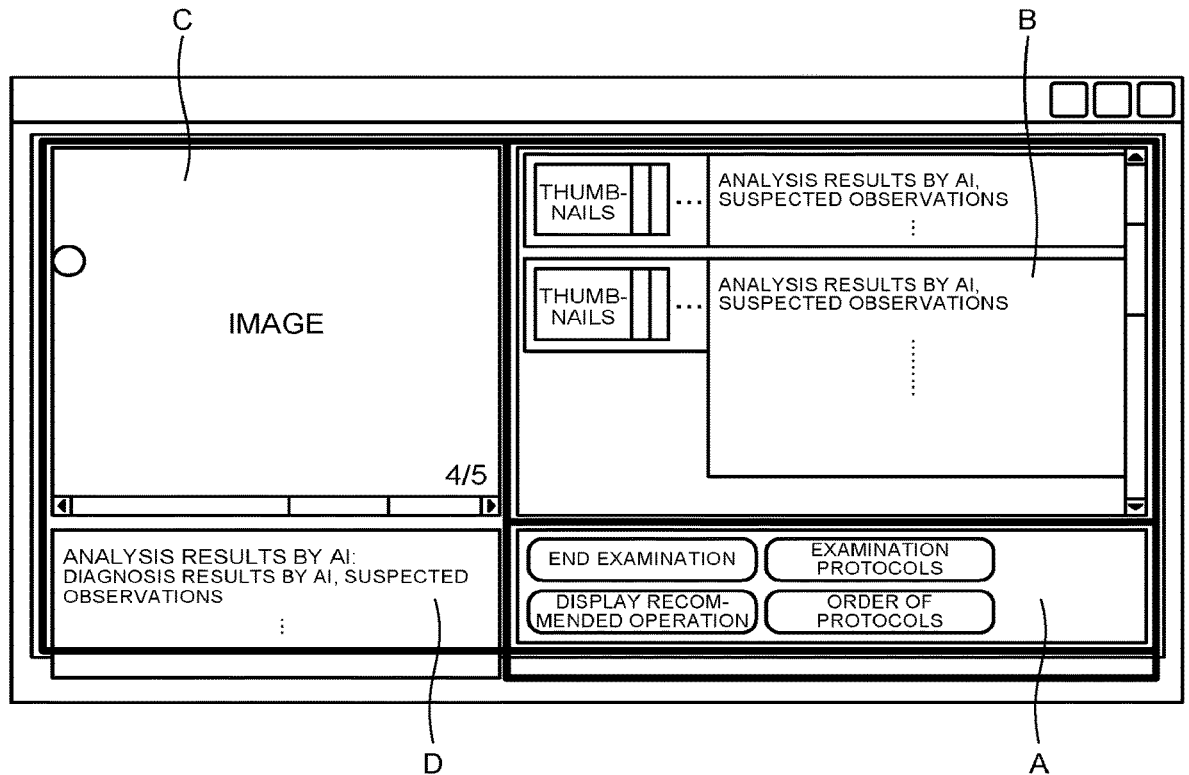
FIG. 4 is a drawing illustrating an example of a Graphical User Interface (GUI) including reference information presented by a display circuit 25 at step S7 in FIG. 2.

FIG. 4 is a drawing illustrating an example of a GUI including the reference information presented by the display circuit 25 at step S7. In FIG. 4, the GUI including the reference information is divided roughly in four regions, for example.

In region A at the bottom right of the GUI, four buttons, namely "END EXAMINATION", "EXAMINATION PROTOCOLS", "DISPLAY RECOMMENDED OPERATION", and "ORDER OF PROTOCOLS" are displayed. The button "END EXAMINATION" is used for ending the examination immediately. This button is displayed in region A when it is determined that the examination "does not need" to be continued, at step S7 where it is judged whether or not the examination needs to be continued. Accordingly, as a result of the "END EXAMINATION" button being displayed in region A, the user is able to learn that the imaging assisting apparatus 30 has determined that the examination protocols include one or more scan protocols that do not need to be executed.

In region A, the button "EXAMINATION PROTOCOLS" is used for causing a list to be displayed, while distinguishing already-executed scan protocols from not-yet-finished scan protocols, among the scan protocols included in the examination protocols. For example, let us discuss a situation where, among the examination protocols illustrated in FIG. 3, while the imaging process according to the scan protocol "Diffusion Weighted Image (DWI)" is being executed, it is determined at step S5 that the examination "does not need" to be continued.

In this situation, when the button "EXAMINATION PROTOCOLS" in region A is pressed, the "Locator", the "Map", and the "Shimming" that have already been finished, as well as the "FLAIR", the "T2-weighted image", and the "MRA" that have not yet been finished are displayed. As for the "Diffusion Weighted Image (DWI)", in the situation where the imaging process according to this scan protocol has all been finished, this scan protocol is displayed as being classified as an already-executed scan protocol, but otherwise this scan protocol is displayed as being classified as a not-yet-finished scan protocol.

In region A, the button "DISPLAY RECOMMENDED OPERATION" is used for causing a recommended condition to be displayed, for example, to increase the contrast of a region subject to a diagnosis process, with respect to a specific scan protocol. Further, when the button "DISPLAY RECOMMENDED OPERATION" is pressed, the recommended operation may be displayed together with a basis thereof. In addition, another arrangement is also acceptable in which sets of protocols adjusted for each site and each symptom are prepared, so that when the button "DISPLAY RECOMMENDED OPERATION" is pressed, an appropriate set of protocols is presented.

In region A, the button "ORDER OF PROTOCOLS" is used for causing information to be displayed in relation to the order of the scan protocols included in the examination protocols.

In region B at the top right of the GUI, thumbnail images of the images obtained by the imaging processes according to the scan protocols, together with image analysis results obtained by AI, observations, and the like are displayed as being classified according to series determined by a Digital Imaging and Communications in Medicine (DICOM) standard. Further, the thumbnail images, the observations, and the like displayed in region B are displayed in the order of the execution of the examinations or according to the level of seriousness of the observations. Further, the displayed images may be images obtained by applying a Maximum Intensity Projection (MIP) to the acquired images or images on which post-processing has been performed by using an arbitrary image processing process.

The series being displayed in region B include the MR images serving as a basis of the determination that the examination "does not need" to be continued, at step S7 where it is judged whether or not the examination needs to be continued. Accordingly, as a result of the thumbnail images corresponding to the series and the like being displayed in region B, the user is able to learn which image was used by the imaging assisting apparatus 30 as a basis of the determination that the examination "does not need" to be continued.

In region C at the top left of the GUI, for example, an image included in a series that is currently being imaged or has recently finished being imaged is displayed. Further, region C may also display an image selected from the thumbnail images, the observations, and the like displayed in region B of the GUI. Alternatively, the thumbnail images, the observations, and the like displayed in region B may be displayed in another window different from region C (e.g., a popup window).

In region D at the bottom left of the GUI, analysis results, suspected observations, and the like regarding the image displayed in region C are displayed. Accordingly, the user is able to view the image displayed in region C, at the same time with the analysis results, the observations, and the like displayed in region D.

Returning to the description of the flowchart in FIG. 2, when an instruction indicating that the examination "needs" to be continued is input via the input circuit 24 in response to the presented reference information (step S8: Yes), the processing circuit 26 continues the imaging processes according to the not-yet-finished scan protocols, by employing the imaging controlling function 26a.

In this situation, when no explicit instruction indicating that the examination "needs" to be continued is input via the input circuit 24, the processing circuit 26 may be configured, when a predetermined time period has elapsed, so as to automatically continue the imaging processes according to the not-yet-finished scan protocols, by employing the imaging controlling function 26a.

On the contrary, when an instruction indicating that the examination "does not need" to be continued is input via the input circuit 24 in response to the presented reference information (step S8: No), the processing circuit 26 deletes the not-yet-finished scan protocols and ends the examination, by employing the imaging controlling function 26a (step S9).

Application Example 1

In magnetic resonance imaging, there are image taking method called Arterial Spin Labeling (ASL) methods. The ASL methods are a type of non-contrast-enhanced image taking methods by which a signal of a fluid (e.g., blood, cerebrospinal fluid, lymph, etc.) flowing into an imaged region is rendered by applying a tag pulse so as to label the fluid. According to an ASL method, blood can be labeled by the application of the tag pulse, so as to render a signal of the blood flowing into an imaged region. Further, the ASL methods include a method by which a background signal other than the signal of the fluid subject to the observation is suppressed by applying a region selective or non-selective pre-pulse, after a tag pulse is applied but before a magnetic resonance signal is acquired.

Inversion Time (TI), which denotes the time period between when a tag pulse is applied and when a magnetic resonance signal is acquired, varies depending on the tissue in the background that is not subject to an observation and is to be suppressed. For this reason, in MR images obtained by using an ASL method, the contrast between the fluid subject to the observation and the other regions changes depending on the timing with which the pre-pulse is applied and TI.

Accordingly, when an examination is performed by using an ASL method, examination protocols may include a plurality of scan protocols having mutually-different combinations of pre-pulse application timing and TI, for example. When imaging processes are performed according to the plurality of scan protocols, there may be a situation where the data necessary for the diagnosis process becomes available without the need to execute the scan protocols of all the combinations. When desired MR images have been obtained with certain scan protocols, and the imaging assisting apparatus 30 determines that the examination does not need to be continued, it is possible to delete the remaining scan protocols, as necessary.

Application Example 2

In magnetic resonance imaging, in the situation where a locator image is taken, and subsequently, a plurality of slice images are taken so as to sequentially generate reconstructed images, when the imaging assisting apparatus 30 determines that the examination does not need to be continued on the basis of a specific slice image, it is possible to finish the imaging processes as necessary and delete the remaining scan protocols. Further, when it is possible to determine that the examination does not need to be continued on the basis of a locator image acquired for a purpose other than the diagnosis purpose, the scan protocols for generating diagnosis images may be deleted.

First Modification Example

In the first embodiment, the example was explained in which the computer system 20 incorporated in the magnetic resonance imaging apparatus 100 has the functions of the imaging assisting apparatus 30. However, the imaging assisting apparatus 30 does not necessarily have to be incorporated in the magnetic resonance imaging apparatus 100. It is also possible to realize the imaging assisting apparatus 30 by using an in-hospital computer or a cloud-type computer connected to the magnetic resonance imaging apparatus 100 via a network, for example.

When this configuration is used, the processes indicated with a broken-line in FIG. 2 correspond to the imaging assisting processes performed by the imaging assisting apparatus 30 according to the first embodiment. The imaging assisting apparatus 30 provided on a server side is configured to successively receive pieces of MR data obtained in the imaging processes, from the magnetic resonance imaging apparatus 100 provided on a client side, so that the processes at steps S3 through S6 in FIG. 2 are performed.

Second Modification Example

In the first embodiment, the example was explained in which, after the reference information is presented at step S7, only when an instruction indicating that the examination "does not need" to be continued is explicitly input by the user via the input circuit 24 at step S8, the not-yet-finished scan protocols are deleted, and the examination is ended.

However, another arrangement is also acceptable in which, when it is determined at step S5 that the examination "does not need" to be continued, the not-yet-finished scan protocols are automatically deleted so that the examination is ended, without presenting the user with the reference information.

Third Modification Example

In the first embodiment, it is judged whether or not the examination needs to be continued by using the MR images that have been image-reconstrued from the MR data. However, another arrangement is also acceptable in which whether or not the examination needs to be continued is judged by using k-space data, instead of the image-reconstructed MR images. This configuration is realized by judging whether or not the examination needs to be continued at step S5, while using a learning model with AI or the like, to which the k-space data is input, for example.

Fourth Modification Example

In the first embodiment, the example was explained in which the imaging assisting apparatus 30 is applied to the magnetic resonance imaging apparatus 100. Alternatively, the imaging assisting apparatus 30 according to the first embodiment is applicable to any medical image diagnosis apparatus configured to execute a plurality of scan protocols during an examination, such as an X-ray computed tomography apparatus.

When the imaging assisting apparatus 30 is applied to an X-ray computed tomography apparatus, whether or not the examination needs to be continued is judged by using projection data or CT images reconstructed from projection data.

Fifth Modification Example

As explained above, it is possible to perform the process of extracting the information related to diseases, by using a learning model. In that situation, the processing circuit 26 may perform the execution of the scan protocols, in parallel with the extraction of the information related to diseases performed by the learning model.

As explained above, the imaging assisting apparatus 30 according to the present embodiment is configured to assist the imaging of the medical image diagnosis apparatus that executes the series of examination protocols including the plurality of scan protocols. The processing circuit 26 is configured to obtain the data acquired according to the one or more already-executed scan protocols among the plurality of scan protocols and to perform one of the following on the basis of the information related to diseases extracted from the obtained data: cancelling the execution of the imaging processes according to the not-yet-finished scan protocols among the plurality of scan protocols; and generating the reference information related to the cancelling of the execution of the imaging processes according to the not-yet-finished scan protocols.

Accordingly, for example, when the presence of a disease or a region suspected of a disease is extracted from the obtained data, it is possible to cancel the imaging processes according to the not-yet-finished scan protocols. Further, because the reference information related to the cancelling of the execution of the imaging processes is presented, the user is able to delete, based on his/her own judgment, the imaging processes according to the not-yet-finished scan protocols, as necessary, by referring to the presented reference information.

With this arrangement, it is possible to omit the wasteful procedure where the images unnecessary for the diagnosis process are obtained by executing the unnecessary scan protocols. It is therefore possible to reduce the total number of images acquired in the scans. Consequently, it is possible to narrow down the images that need to be viewed by the interpreter doctor, compared to conventional examples. It is therefore possible to reduce the burden on the interpreter doctor.

For example, in the situations (e.g., when a patient suspected of a cerebral infarction is urgently carried in) where it is necessary to identify the infarction site as soon as possible and to determine the next procedure, it is possible to execute required minimum scan protocols, so as to promptly start the treatment, without performing the imaging processes according to the unnecessary scan protocols. As a result, it is possible to promptly provide the medical doctor and/or the medical technologist with effective information, without excess or insufficiency.

Second Embodiment

Next, the imaging assisting apparatus 30 according to a second embodiment will be explained. The imaging assisting apparatus 30 according to the present embodiment is an imaging assisting apparatus configured to assist imaging of a medical image diagnosis apparatus that executes one scan protocol of which the image taking parameter dynamically changes.

The processing circuit 26 included in the imaging assisting apparatus 30 according to the present embodiment is configured, by employing the examination continuation judging function 26b, to obtain data acquired up to a certain stage in the execution of the one scan protocol and to perform one of the following on the basis of information related to diseases extracted from the obtained data: cancelling the data acquisition that is scheduled in the one scan protocol but has not yet been executed; and generating reference information related to cancelling the data acquisition.

Figure 5:
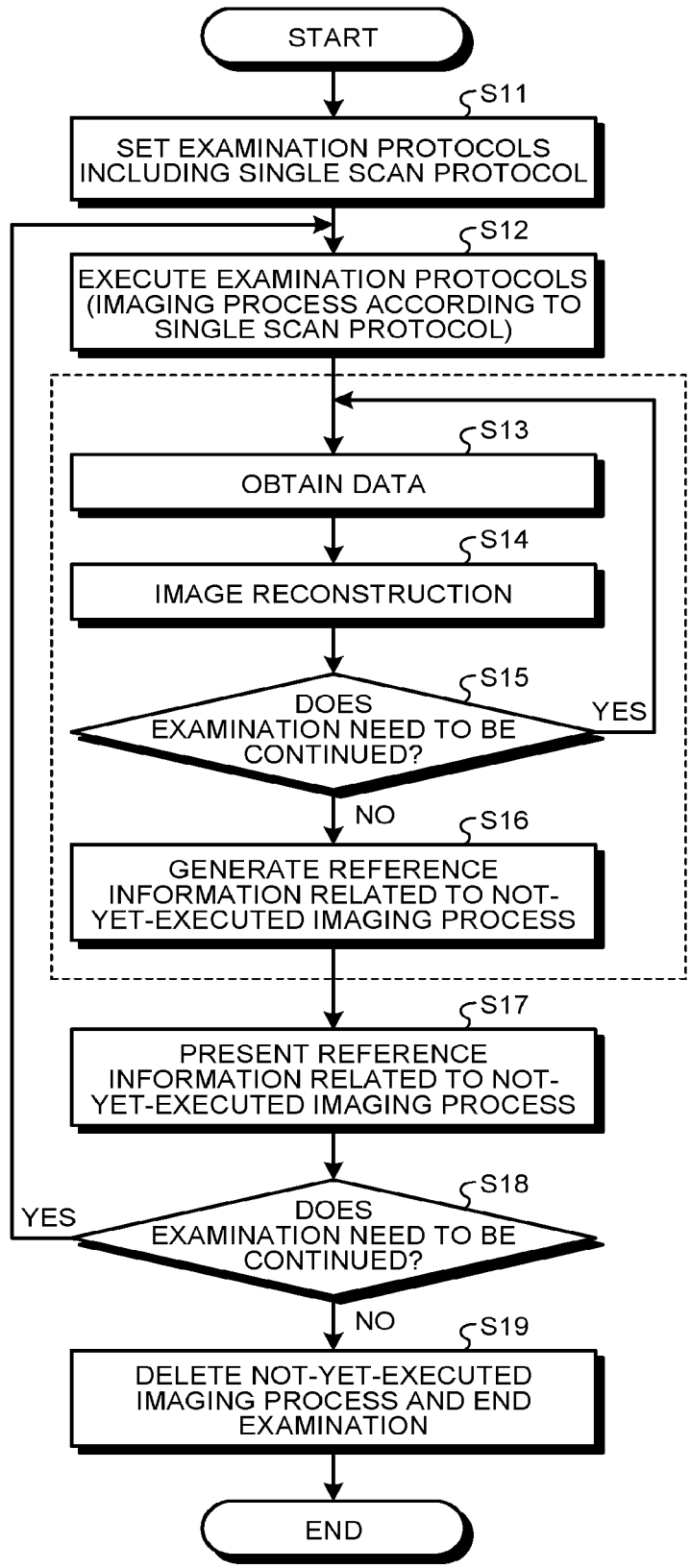
FIG. 5 is a flowchart illustrating an example of a flow in an imaging assisting process performed on the magnetic resonance imaging apparatus 100 by the imaging assisting apparatus 30 according to a second embodiment.

FIG. 5 is a flowchart illustrating a flow in an imaging assisting process performed on the magnetic resonance imaging apparatus 100 by the imaging assisting apparatus 30 according to the second embodiment.

As illustrated in FIG. 5, to begin with, on the basis of an input from the input circuit 24, the processing circuit 26 sets examination protocols by employing the imaging controlling function 26a (step S11).

Figures 6, 7:
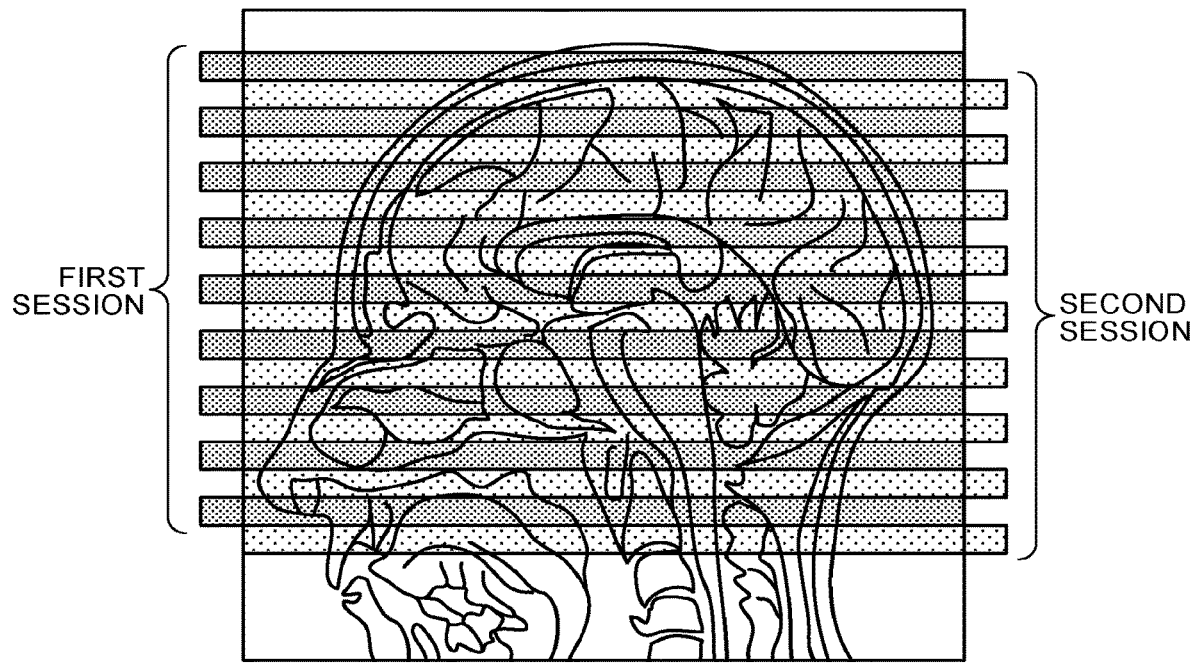
FIG. 6 is a drawing illustrating examples of examination protocols set at step S11 in FIG. 5.
FIG. 7 is a drawing for explaining an example of an image taking method using an interleave scheme.

FIG. 6 is a drawing illustrating examples of the examination protocols set at step S11 in FIG. 5. In FIG. 5, the "protocol a" is the name of one scan protocol of which the image taking parameter dynamically changes. For example, the "protocol α" is a protocol defining a pulse sequence in which the sampling density is gradually increased for the k-space data to be obtained for the purpose of generating diagnosis images. In another example, the "protocol α" is a protocol defining a pulse sequence in which, at the beginning, k-space data is sampled with a low resolution with a small matrix size, so that the resolution is gradually increased by enlarging the matrix size. In yet another example, the "protocol α" is a protocol defining a pulse sequence in which, at the beginning, k-space data is sampled with a setting of a large slice thickness, so that the slice thickness is gradually reduced.

After that, by employing the imaging controlling function 26a, the processing circuit 26 sequentially performs the imaging processes according to the examination protocols set at step S11 (step S12).

For example, in the example in FIG. 6, by employing the imaging controlling function 26a, the processing circuit 26 obtains information necessary for the acquisitions and corrections of the diagnosis images, by executing the "Locator", the "Map", and the "Shimming" in the stated order and further takes the diagnosis images on the basis of the "protocol α".

The image reconstructing circuit 22 sequentially obtains pieces of MR data acquired through the imaging processes executed at step S12 (step S13) and generates MR images by performing an image reconstructing process (step S14).

Subsequently, by employing the examination continuation judging function 26b, the processing circuit 26 sequentially receives the reconstructed MR images from the image reconstructing circuit 22 and judges whether or not the examination needs to be continued, by using the received MR images (step S15).

When it is determined that the examination "needs" to be continued (step S15: Yes), the processing circuit 26 returns to step S13.

On the contrary, when it is determined that the examination "does not need" to be continued (step S15: No), the processing circuit 26 generates reference information related to the one or more not-yet-executed imaging processes (step S16). More specifically, the processing circuit 26 generates, by employing the examination continuation judging function 26b, reference information related to cancelling the data acquisition that is scheduled in the scan protocol α but has not yet been executed. Further, by employing the display controlling function 26c, the processing circuit 26 presents the reference information related to the one or more not-yet-executed imaging processes (step S17). More specifically, the processing circuit 26 presents the generated reference information via the display circuit 25.

For example, let us discuss an example in which, according to the scan protocol α illustrated in FIG. 6, while imaging processes are repeatedly performed by changing the matrix size at stages from 256×256 to 1,024×1,024, it is determined that an MR image reconstructed on the basis of the data acquired with the matrix size of 512×512 is sufficient for the diagnosis process and determined at step S15 that the examination "does not need" to be continued. In this situation, as for the data acquisition with the matrix size of 1,024×1,024 that has not yet been executed, it is determined that the examination "does not need" to be continued.

In another example, when a "Diffusion Weighted Image (DWI)" is taken for the purpose of judging whether or not it is necessary to inject a tissue Plasminogen Activator (tPA) into a vein to promote dissolution of blood clots in an infarction site, or when an MR image is used for checking to see whether or not brain hemorrhage is occurring during intraoperative MRI, it may be possible, in some situations, to determine whether or not the procedure is necessary even with not so large a matrix size. Accordingly, when an MR image obtained from the imaging process with a small matrix size is determined to be sufficient for the diagnosis process, and it is determined that the examination does not need to be continued, the scheduled imaging process with a large matrix size is cancelled. Consequently, because the procedure is limited to the required minimum imaging process, it is possible to promptly proceed to the surgical procedure such as injecting tPA into a vein or draining blood with craniotomy.

In response to the presented reference information, when an instruction indicating that the examination "needs" to be continued is input via the input circuit 24 (step S18: Yes), the processing circuit 26 continues to execute the not-yet-executed data acquisition according to the protocol α, by employing the imaging controlling function 26a.

When no explicit instruction indicating that the examination "needs" to be continued is input via the input circuit 24, the processing circuit 26 may be configured, when a predetermined time period has elapsed, so as to continue the not-yet-executed data acquisition according to the scan protocol α, by employing the imaging controlling function 26a.

On the contrary, when an instruction indicating that the examination "does not need" to be continued is input via the input circuit 24 in response to the presented reference information (step S18: No), the processing circuit 26 deletes the not-yet-executed imaging process and ends the examination. More specifically, the processing circuit 26 cancels the not-yet-executed data acquisition according to the scan protocol a and ends the examination, by employing the imaging controlling function 26a (step S19).

Third Application Example

For example, let us discuss an example in which, during an examination using a thinning-out imaging process called Parallel Imaging (PI) or Compressed Sensing (CS), a pulse sequence is executed by which the sampling density is gradually increased in one scan protocol. For example, when the imaging process is performed while changing the thinning-out ratio or the compression ratio from 1/4 to 1/3 and to 1/2, and an MR image obtained with the thinning-out ratio or the compression ratio of 1/3 in the interim is determined to be sufficient for the diagnosis process, it is determined that the examination does not need to be continued. It is therefore possible to cancel the execution of the scan protocol without performing the following data acquisition with the thinning-out ratio or the compression ratio of 1/2.

Fourth Application Example

For example, let us discuss an example in which a scan protocol is executed by which an imaging process is performed at the beginning with a rather large slice thickness with a low resolution, so that that slice thickness is gradually reduced so as to realize a higher resolution. For example, when a pulse sequence is executed by which the slice thickness is changed from 7 mm to 5 mm, and to 3 mm, and an MR image obtained with the slice thickness of 5 mm is determined to be sufficient for the diagnosis process, it is determined that the examination does not need to be continued. It is therefore possible to cancel the execution of the scan protocol, without performing the following data acquisition with the slice thickness of 3 mm.

Fifth Application Example

For example, let us discuss an example in which multi slices are acquired from an imaged region by implementing an interleave scheme. FIG. 7 is a drawing for explaining an example of an image taking method using the interleave scheme. According to the image taking method using the interleave scheme, to suppress crosstalk of RF pulses between adjacent slices, the acquisition is divided into multiple sessions, so that the slice positions of the acquisitions in each session are set at intervals. In the example in FIG. 7, the group of slices acquired over the two sessions is arranged so as to complementarily satisfy the number of slices set for the FOV.

In such an imaging process using the interleave scheme, when it is determined, for example, that an MR image resulting from reconstruction of the data acquired in the first session is determined to be sufficient for the diagnosis process and that the examination does not need to be continued, it is possible to cancel the acquisition in the second session. In other words, although the MR image resulting from the reconstruction of the data acquired in the first session has a smaller amount of information than that of the scheduled MR images, the imaging process in the second session may be omitted as long as the information is sufficient for the diagnosis process.

As explained above, the imaging assisting apparatus 30 according to the present embodiment is configured to assist the imaging of the medical image diagnosis apparatus that executes the scan protocol of which the image taking parameter dynamically changes in the one scan protocol. The processing circuit 26 is configured to obtain the data acquired up to a certain stage in the execution of the scan protocol and to perform one of the following on the basis of the information related to diseases extracted from the obtained data: cancelling the data acquisition that is scheduled in the scan protocol but has not yet been executed; and providing the reference information related to the cancelling of the data acquisition.

Accordingly, it is possible to realize the same advantageous effects as those of the first embodiment, with the medical image diagnosis apparatus that executes the scan protocol of which the image taking parameter dynamically changes in one scan protocol.

According to at least one aspect of the embodiments described above, it is possible to assist the imaging to shorten the image interpretation period or the examination period.

The term "processor" used in the explanations of the above embodiments denotes, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the storage circuit 23. Alternatively, instead of saving the programs in the storage circuit 23, it is also acceptable to directly incorporate the programs in the circuits of the one or more processors. In that situation, the one or more processors realize the functions by reading and executing the programs incorporated in the circuits thereof.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An imaging assisting apparatus comprising a processing circuit configured to:
    set an examination protocol including a first scan protocol and a second scan protocol whose type is different from the first scan protocol;
    obtain data acquired according to the first scan protocol included in the set examination protocol;
    display information including a plurality of unfinished scan protocols and an analysis result of the data on a display screen, and receive from a user a selection of a scan protocol to be executed and a scan protocol not to be executed from among the plurality of unfinished scan protocols displayed on the display screen, the plurality of unfinished scan protocols being included in the set examination protocol; and
    display a list including all of the plurality of unfinished scan protocols, and an inquiry to a user about each of the plurality of unfinished scan protocols in the list, the inquiry being whether or not to delete a respective one of the plurality of unfinished scan protocols.

2. The imaging assisting apparatus according to claim 1, wherein the processing circuit is further configured to display, on the display screen, necessity or unnecessity to execute imaging according to the second scan protocol and reference information used by a user for judging whether imaging according to the second scan protocol continues to be executed.

3. The imaging assisting apparatus according to claim 1, wherein the second scan protocol includes a protocol for generating a diagnosis image.

4. The imaging assisting apparatus according to claim 3, wherein
    the data includes the diagnosis image, and
    the processing circuit is further configured to detect the disease or the region suspected of the disease from the diagnosis image.

5. The imaging assisting apparatus according to claim 3, wherein
    the data includes a locator image referenced for determining an acquisition region of the diagnosis image, and
    the processing circuit is further configured to detect the disease or the region suspected of the disease from the locator image.

6. The imaging assisting apparatus according to claim 1, wherein the first scan protocol or the second scan protocol includes a plurality of scan protocols having mutually-different Inversion Time values for a pulse used for labeling fluid according to an Arterial Spin Labeling (ASL) method.

7. The imaging assisting apparatus according to claim 1, wherein the analysis result corresponds to a result that is obtained by performing an analysis process on an image based on the data.

8. A magnetic resonance imaging apparatus comprising the imaging assisting apparatus according to claim 1.

9. The imaging assisting apparatus according to claim 1, wherein the processing circuit is further configured to display information including the plurality of unfinished scan protocols and the analysis result of the data on the display screen after the first scan protocol has been finished and before the set examination protocol is finished.

10. The imaging assisting apparatus according to claim 1, wherein the processing circuit is further configured to receive from the user an instruction to display a recommended operation, and, in response to receiving the instruction, display a recommended condition to increase a contrast of a region subject to a diagnosis process with respect to a specific scan protocol from among the plurality of scan protocols.

11. The imaging assisting apparatus according to claim 1, wherein the processing circuit is further configured to display thumbnail images of images obtained by imaging processes according to one or more of the plurality of scan protocols, together with image analysis results obtained by observations of the obtained images, wherein the thumbnail images and the image analysis results are displayed in an order according to a level of seriousness of the observations.

12. A non-transitory computer-readable storage medium storing therein instructions that cause a computer to execute:
    setting an examination protocol including a first scan protocol and a second scan protocol whose type is different from the first scan protocol;
    obtaining data acquired according to the first scan protocol included in the set examination protocol;
    displaying information including a plurality of unfinished scan protocols and an analysis result of the data on a display screen, and receiving from a user a selection of a scan protocol to be executed and a scan protocol not to be executed from among the plurality of unfinished scan protocols displayed on the display screen, the plurality of unfinished scan protocols being included in the set examination protocol; and
    displaying a list including all of the plurality of unfinished scan protocols, and an inquiry to a user about each of the plurality of unfinished scan protocols in the list, the inquiry being whether or not to delete a respective one of the plurality of unfinished scan protocols.

13. The non-volatile and non-transitory computer-readable storage medium according to claim 12, wherein the instructions further cause the computer to further execute displaying, on the display screen, necessity or unnecessity to execute imaging according to the second scan protocol and reference information used by a user for judging whether imaging according to the second scan protocol continues to be executed.

14. An imaging assisting system comprising:
an image assisting apparatus including a processing circuit configured to:
set an examination protocol including a first scan protocol and a second scan protocol whose type is different from the first scan protocol;
obtain data acquired according to the first scan protocol included in the set examination protocol;
analyze an image based on the data to generate an analysis result corresponding to the data;
display information including a plurality of unfinished scan protocols and an analysis result of the data on a display screen, and receive from a user a selection of a scan protocol to be executed and a scan protocol not to be executed from among the plurality of unfinished scan protocols displayed on the display screen, the plurality of unfinished scan protocols being included in the set examination protocol; and
display a list including all of the plurality of unfinished scan protocols, and an inquiry to a user about each of the plurality of unfinished scan protocols in the list, the inquiry being whether or not to delete a respective one of the plurality of unfinished scan protocols.

15. An imaging assisting method comprising:
setting an examination protocol including a first scan protocol and a second scan protocol whose type is different from the first scan protocol;
obtaining data acquired according to the first scan protocol included in the set examination protocol;
analyzing an image based on the data to generate an analysis result corresponding to the data;
displaying information including a plurality of unfinished scan protocols and an analysis result of the data on a display screen, and receiving from a user a selection of a scan protocol to be executed and a scan protocol not to be executed from among the plurality of unfinished scan protocols displayed on the display screen, the plurality of unfinished scan protocols being included in the set examination protocol; and
displaying a list including all of the plurality of unfinished scan protocols, and an inquiry to a user about each of the plurality of unfinished scan protocols in the list, the inquiry being whether or not to delete a respective one of the plurality of unfinished scan protocols.

\* \* \* \* \*